Feb. 5, 1974 R. L. BYRUM Plant Pat. 3,468
ROSE PLANT
Filed July 26, 1972
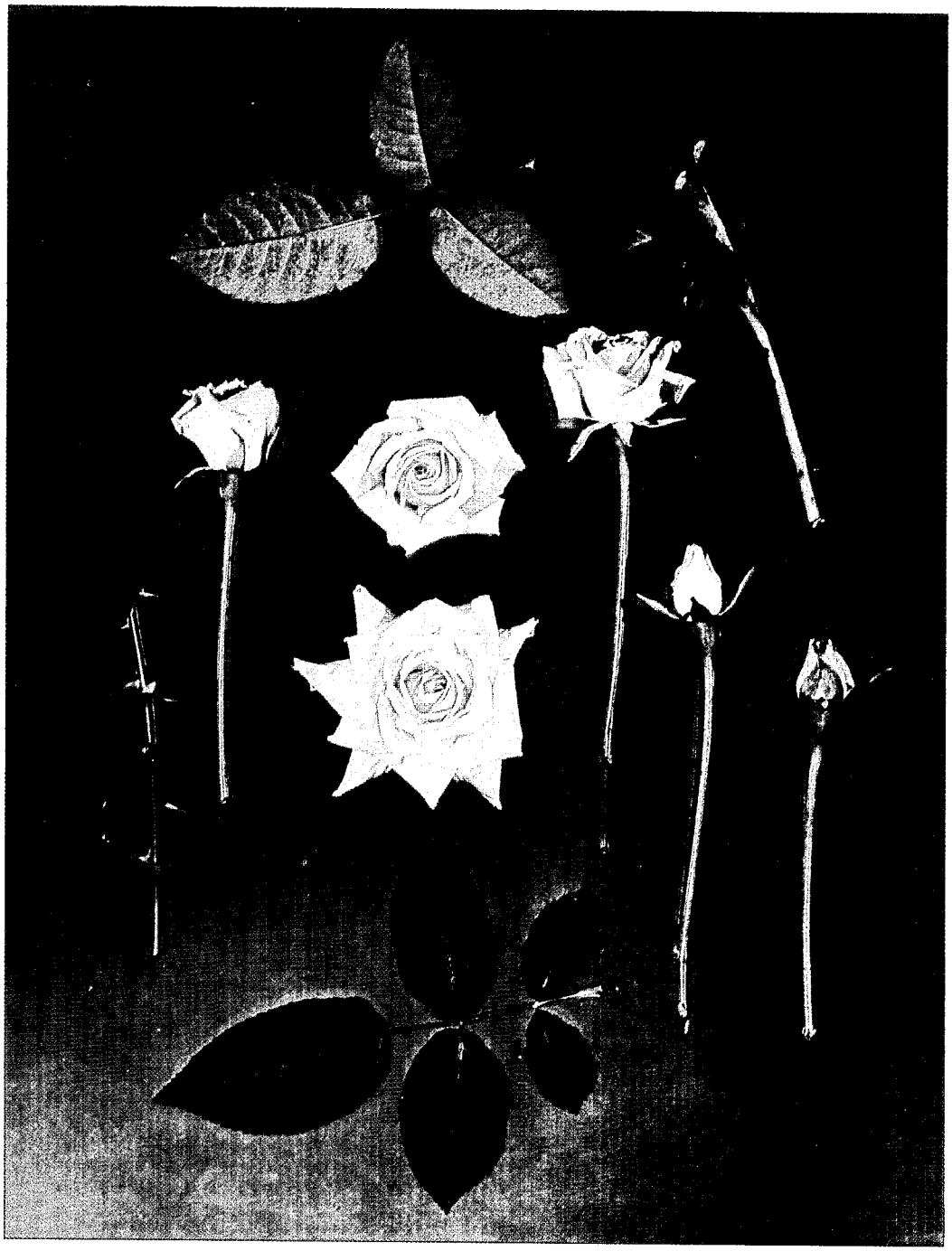

United States Patent Office

Plant Pat. 3,468
Patented Feb. 5, 1974

3,468

ROSE PLANT

Roy L. Byrum, Richmond, Ind., assignor to Joseph H. Hill Company, Richmond, Ind.

Filed July 26, 1972, Ser. No. 275,361
Int. Cl. A01h *5/00*
U.S. Cl. Plt.—26 1 Claim

ABSTRACT OF THE DISCLOSURE

A new variety of greenhouse rose plant distinguished by its free and vigorous growing habit, consistency of propagation, abundant production, profuse lush green foliage and flowers of a lighter, more iridescent pink which have excellent keeping qualities.

BACKGROUND OF THE INVENTION

This new variety of rose plant was developed in the course of a breeding program carried on by me at Richmond, Ind., with the primary object of improving the character and quality of greenhourse rose plants for the commercial production of cut flowers, and is the result of a crossing of Seventeen (P.P. 1,765) with Jack Frost (P.P. 2,447) made by me in the spring of 1966. This crossing, among others for the same purpose, was done in the hope of finding improved varieties of pink roses and this resulting seedling, upon flowering in the fall of 1967, was found to have a number of distinctive and advantageous characteristics which, if retained, would have considerable value. A particular characteristic of this new variety, in addition to its vigorous growth habit, abundant production and consistency of propagation, features a profuse lush green foliage making it easier to arrange for all occasions and a flower having a lighter, more iridescent pink color and excellent keeping qualities, very different from the flower of either of its parents, and for that reason it was selected for propagation and test.

Asexual propagation of this new variety of rose plant was done under my direction at Hamilton City, Calif., by budding, and subsequent propagations have proven that the distinctive characteristics of this new variety of rose plant hold true through succeeding propagations from generation to generation.

DESCRIPTION OF THE DRAWING

This new variety of rose plant is illustrated by the accompanying drawing which, in full color as closely true as is reasonably possible by conventional color reproduction processes, shows the form of the newly opened flower, very young wood with new leaves, mature wood, buds in several stages of opening, and the upper and under sides of typical mature leaves.

DESCRIPTION OF THE NEW PLANT

The following is a detailed description of my new variety of rose plant, with color designations according to Koster's Color Guide (K) and Robert S. Wilson's Horticultural Colour Chart (W), based upon observations made at Richmond, Ind., in 1971.

*The plant*

Origin: Seedling (67–35P)
Parentage:
Seed parent—Seventeen (P.P. 1,765)
Pollen parent—Jack Frost (P.P. 2,447)
Classification: Floribunda
Form: Bush
Habit: Much branched
Growth: Free and vigorous Main stems: Color—Spinach Green 0960/2 (W)
*Thorns.*—Several, of medium length, hooked downwardly from a short round base. Color—Dark Violet, Plate No. 58 (K)
*Prickles and hairs.*—None
Branches: Color—Spinach Green 0960/2 (W)
*Thorns.*—Several, of medium length, hooked downwardly from a short base. Color—nearest color Deep Carmine Violet, Plate No. 46 (K)
*Prickles and hairs.*—None
New shoots: Color—Pod Green 061/2 (W) overlaid with Magenta, Plate No. 50 (K), on parts of stem
*Thorns.*—Several, medium length, straight from a short, narrow base. Color—Rose Opal 022/2 (W) at base gradually changing to Rose Opal 022/3 (W) at tip
*Prickles and hairs.*—None
Foliage:
*Leaves.*—3 to 5 in number, Quantity—abundant. Size—medium to large. Shape—odd pinnate. Aspect—moderately heavy
*Leaflets.*—Shape—ovoid with round base, acute apex, and simply serrate margin. Color: Young, upper side—Pod Green 061/2 (W) overlaid with Purple Madder 1028/2 (W). Young, under side—Pod Green 061/3 (W) overlaid with Purple Madder 1028/3 (W) mostly around outer edge of petal. Mature, upper side—Nearest color Spinach Green 0960 (W) with edge of leaves showing a slight tinge of Dark Purple, Plate No. 56 (K). Mature, under side—Nearest color Sage Green 000861/1 (W)
*Rachis.*—Medium heavy, with grooved upper side and prickly under side
*Stipules.*—Medium length and medium width, with medium length points turning outwardly at an angle of less than 45°

*The bud*

Before calyx breaks:
*Size.*—Medium small
*Form.*—Short pointed with a conspicuous neck and with foliaceous appendages on the surface of the bud having much cut parts extending beyond tip of bud a distance equal to one quarter or more of the bud length
*Color of calyx.*—Scheeles Green 860/3 (W)
As calyx breaks:
*Color.*—Outer side of petal—Phlox Pink 625/3 (W) in center of petal gradually changing to Phlox Pink 625/2 (W) at edge of petal
As first petal opens:
*Size.*—Medium small
*Form.*—Short-pointed
*Color.*—Outside—Shades of Phlox Pink 625/3 (W) and 625/3 (W) with base of petal Mimosa Yellow 602/3 (W). Inside—Phlox Pink 625/1 (W) with base of petal Mimosa Yellow 602/3 (W)
*Bud opening.*—Bud opens up well in greenhouse. No unusual characteristics noted as to effect of cold, hot, wet or dry weather on opening.
Sepals: Permanent, spear shaped, medium length
*Color.*—Inside surface—Scheeles Green 860/3 (W) overlaid with white fuzz. Outside surface—Scheeles Green 860/3 (W)
Peduncle: Medium length, medium diameter and erect
*Bark of peduncle.*—Smooth. Color—Scheeles Green 860 (W)
*Thorns.*—None
*Hairs and prickles.*—None

*The flower*

Blooming habit: Abundant and continuous
Size: Medium—1½ to 2½ inches in diameter
Borne: Singly to a stem on moderately strong stems of medium length
Form: Full and high centered at first, becoming more high centered as flower matures. Petals remain tightly rolled outwardly at first, remaining tightly rolled outwardly at maturity
Petalage: Very double, with 40 to 45 petals arranged regularly
*Shape of petals.*—Outside—Obovate, with retuse apex. Intermediate—Obovate, with retuse apex. Inside—Obovate and some spatulate with retuse apex and few with one notch
*Texture.*—Moderately thick
*Appearance.*—Inside—satiny. Outside—shiny Color of a newly opened flower in greenhouse October 1971:

Outside petals

Outer surface—Rose Pink 427/3 (W)
Inner surface—Rose Pink 427/1 (W) with veins of Rhodamine Pink 527/2 (W)

Intermediate and inner petals

Outside surface—Rose Pink 427/2 (W) with base of petal Empire Yellow 603/3 (W)
Inside surface—Rhodamine Pink 527/2 (W) with base of petal Empire Yellow 603/3 (W)

Color of a flower opened for three days October 1971:

Outside petals

Outer surface—White overlaid with Rose Pink 427/3 (W)
Inner surface—White overlaid with Rose Pink 427/2 (W)

Intermediate and inner petals

Outside surface—White overlaid with Rose Pink 427/3 (W)
Inside surface—White overlaid with Rose Pink 427/2 (W)

General color effect of the open bloom:

*Newly opened flower*—Rose Pink 427/1 (W)
*Three days opened flower*—Rose Pink 427/2 (W)

Persistence: Petals persist
Fragrance: Slight Tea
Lasting quality: 5 to 6 days in October 1971 and at living room temperature Reproductive organs Stamens: Medium in number arranged regularly about pistils
*Filaments.*—Short in length, most with anthers. Color—Chrome Yellow 605/3 (W)
*Anthers.*—Small to large in size—all open at once. Color—Chrome Yellow 605/2 (W)
*Pollen.*—Moderately abundant. Color—Straw Yellow 604/3 (W)
Pistils: Medium in number
*Styles.*—Uneven medium length, moderately thin and bunched. Color—Shades of Phlox Pink 625/2 (W) through Phlox Pink 625/3 (W)
*Stigmas.*—*Color*—Pure White Plate No. 1 (K)
Ovularies: Some protruding from calyx
Hips: None
Seeds: None This new variety of rose plant is particularly notable because of its remarkable propagation characteristic, which is more successful than the seed parent, and its exceptionally good cut flower production. It is better than its pollen parent in that it has better production and is enirely different in color. This seedling is a prolific grower which supersedes the growth habits of both the seed and pollen parents. It compares with its seed parent Seventeen, Plant Pat. 1765; however, since Seventeen is unable to be propagated with any degree of consistency and the fact that the color of this flower is a more iridescent shade of pink makes it a more profitable commercial rose to grow.

A most distinctive feature of this rose plant is the manner of development of the flower. It commences from a high centered bud with each petal having a pronounced reflux which is a dominant factor in the fully open flower. It has profuse lush green foliage making it easier to arrange from all occasions and it has excellent keeping qualities.

I claim:

1. A new and distinct variety of rose plant substantially as herein shown and described, characterized by its vigorous growth, consistency of propagation, its abundant production of flowers having an iridescent shade of pink color and which develop from a high centered bud with each petal having a pronounced reflux, and by its profuse lush green foliage.

No references cited.

ROBERT E. BAGWILL, Primary Examiner